(12) United States Patent
Qasem (10) Patent No.: US 9,974,450 B2
(45) Date of Patent: May 22, 2018

(54) MEASURING CENTRAL PRESSURE WITH BRACHIAL CUFF

(71) Applicant: AtCor Medical Pty Ltd, West Ryde, NSW (AU)

(72) Inventor: Ahmad M. Qasem, Guildford (AU)

(73) Assignee: ATCOR MEDICAL PTY LTD (AU)

( * ) Notice: Subject to any disclaimer, the term of this patent is extended or adjusted under 35 U.S.C. 154(b) by 0 days. days.

(21) Appl. No.: 15/077,371

(22) Filed: Mar. 22, 2016

(65) Prior Publication Data
US 2016/0198959 A1     Jul. 14, 2016

Related U.S. Application Data

(63) Continuation of application No. 13/101,193, filed on May 5, 2011, now Pat. No. 9,314,170.
(Continued)

(51) Int. Cl.
*A61B 5/02* (2006.01)
*A61B 5/0225* (2006.01)
(Continued)

(52) U.S. Cl.
CPC .......... *A61B 5/0225* (2013.01); *A61B 5/022* (2013.01); *A61B 5/7225* (2013.01); *A61B 5/742* (2013.01); *A61B 2560/0223* (2013.01)

(58) Field of Classification Search
CPC ..... A61B 5/022; A61B 5/02007; A61B 5/021; A61B 5/02; A61B 5/02108; A61B 5/02225; A61B 5/7257; A61B 5/7253
See application file for complete search history.

(56) References Cited

U.S. PATENT DOCUMENTS

| | | | | |
|---|---|---|---|---|
| 4,796,184 A | * | 1/1989 | Bahr | A61B 5/02225 600/492 |
| 5,265,011 A | | 11/1993 | O'Rourke | |

(Continued)

FOREIGN PATENT DOCUMENTS

| | | |
|---|---|---|
| EP | 1179318 | 2/2002 |
| EP | 2070472 | 6/2009 |

(Continued)

OTHER PUBLICATIONS

Roman, Mary J. MD et al., High Central Pulse Pressure is Independently Associated with Adverse Cardiovascular Outcome, Journal of American College of Cardiology, vol. 54, No. 18, Oct. 27, 2009, pp. 1730-1734.
(Continued)

*Primary Examiner* — Patricia Mallari
*Assistant Examiner* — Karen Toth
(74) *Attorney, Agent, or Firm* — Andrus Intellectual Property Law, LLP (57) ABSTRACT

A method for determining a calibrated aortic pressure waveform from a brachial cuff waveform involves the use of one or more generalized transfer functions. The one or more generalized transfer functions are specific for predetermined brachial cuff pressure ranges, such as below diastolic pressure, between diastolic and systolic pressure, and above systolic pressure. The brachial cuff is inflated to a pressure within the pressure range appropriate for the generalized transfer function to be applied to the brachial cuff waveform to generate the aortic pressure waveform. In some circumstances, it may be necessary to use a calibration transfer function to generate a calibrated aortic waveform. In other circumstances, the calibration transfer function is not necessary.

15 Claims, 5 Drawing Sheets

Related U.S. Application Data (60) Provisional application No. 61/332,224, filed on May 7, 2010.

(51) Int. Cl.
  *A61B 5/00* (2006.01)
  *A61B 5/022* (2006.01)

(56) References Cited

U.S. PATENT DOCUMENTS

| | | | |
|---|---|---|---|
| 5,882,311 | A | 3/1999 | O'Rourke |
| 6,485,431 | B1 | 11/2002 | Campbell |
| 6,647,287 | B1 | 11/2003 | Peel et al. |
| 6,994,675 | B2 | 2/2006 | Sharrock |
| 7,727,157 | B2 | 6/2010 | Sharrock |
| 8,821,403 | B2 | 9/2014 | Sharrock |
| 2002/0156382 | A1 | 10/2002 | Freund et al. |
| 2002/0177781 | A1 | 11/2002 | Amano |
| 2003/0220584 | A1 | 11/2003 | Honeyager et al. |
| 2004/0059231 | A1 | 3/2004 | Narimatso et al. |
| 2008/0287793 | A1 | 11/2008 | Hoffman |
| 2009/0149763 | A1 | 6/2009 | Chen et al. |
| 2009/0287097 | A1 | 11/2009 | Lowe |
| 2010/0152593 | A1 | 6/2010 | Lowe |
| 2010/0241013 | A1 | 9/2010 | Hatib |
| 2011/0237961 | A1 | 9/2011 | Voss et al. |
| 2011/0270098 | A1* | 11/2011 | Chowienczyk .... A61B 5/02116 600/500 |
| 2014/0158162 | A1 | 8/2014 | Narimatsu |

FOREIGN PATENT DOCUMENTS

| | | |
|---|---|---|
| WO | 2007053868 | 5/2007 |
| WO | 2010002250 | 1/2010 |
| WO | 2010058169 | 5/2010 |

OTHER PUBLICATIONS

McEniery, Carmel M. et al., Central Pressure Variability and Impact of Cardiovascular Risk Factors, The Anglo-Cardiff Collaborative Trial II, Hypertension, Jun. 2008, pp. 1476-1482.

Williams, Bryan MD et al., Differential Impact of Blood Pressure-Lowering Drugs on Central Aortic Pressure and Clinical Outcomes, Principal Results of the Conduit Artery Function Evaluation (CAFE) Study, Circulation, Mar. 7, 2006, pp. 1213-1225.

Pauca, Alfredo L. et al., Prospective Evaluation of Methon of Estimating Ascending Aortic Pressure from the Radial Artery Pressure Waveform, Hypertension, Oct. 2001, vol. 38, pp. 932-937.

Sharman, James E. et al., Validation of a Generalized Transfer Function to Noninvasively Derive Central Blood Pressure During Exercise, Hypertension, Jun. 2006, vol. 47, pp. 1203-1208.

Wassertheurer, S. et al., A new oscillometric method for pulse wave analysis: comparison with a common tonometric method, Journal of Human Hypertension 24, 2010, pp. 498-504, published online Mar. 18, 2010.

Jilek et al., Amplitude envelope slopes of oscillometric blood pressure waveforms as defined by amplitude ratios, Applied Electronics, 2009, pp. 137-140.

Mersich et al., Identification of the cuff transfer function increases indirect blood pressure measurement accuracy; Physiological Measurement, Institute of Physics Publishing, Bristol, GB, vol. 30, No. 3, Mar. 1, 2009 pp. 323-333.

Supplementary European Search Report in pending family European Application 11 77 7336 dated Oct. 30, 2017.

* cited by examiner

MEASURING CENTRAL PRESSURE WITH BRACHIAL CUFF

CROSS REFERENCE TO RELATED APPLICATIONS

This application is a continuation of U.S. patent application Ser. No. 13/101,193, filed May 5, 2011, which claims priority from U.S. Provisional Application 61/332,224, filed May 7, 2010.

BACKGROUND OF THE INVENTION

The aortic pressure waveform results from a coupling of cardiac and vascular functions. The combined effects form a waveform shape that reflects the status of the cardiovascular system. The size and shape of the aortic pulse is affected by cardiac output, arterial stiffness and left ventricular (LV) function. Measuring aortic pressure will provide a useful diagnostic tool to the cardiovascular system. The only direct method to measure aortic pressure is through an invasive procedure, which includes inserting a catheter with either a pressure sensor on the tip or a fluid-filled catheter connected to an external pressure sensor located on the electronic module. The method not only increases the risk to the patient, but is cumbersome, intrusive, and a time-consuming procedure that requires significant use of hospital facilities and staff.

A non-invasive and easy alternative is to use a conventional blood pressure cuff sphygmomanometer or any equivalent electronic device to measure the brachial pressure as an indicator for aortic pressure and cardiovascular risk. However, this measurement disregards basic cardiovascular hemodynamic principles: that the pressure waveform amplifies and changes in shape as it travels from the aorta to brachial artery. The changes are due to the difference in arterial properties between the two arterial locations and the influence of wave reflections in the arterial tree. See, Wilmer Nichols, Michael O'Rourke, McDonald's Blood Flow In Arteries: Theoretical, Experimentation and Clinical Principles, 5$^{th}$ Edition, Hodder Arnold, 2005. As a result, the brachial systolic pressure is exaggerated compared to that in the ascending aorta and, therefore, not indicative of cardiac afterload. The consequence of this difference in systolic pressure is demonstrated in numerous studies in which brachial pressure is not indicative of cardiovascular risk when compared to aortic pressure. See, Mary J. Roman, Richard B. Devereux, Jorge R. Kizer, Peter M. Okin, Elisa T. Lee, PHD, Wenyu Wang, Jason G. Umans, Darren Calhoun, Barbara V. Howard, High Central Pulse Pressure Is Independently Associated With Adverse Cardiovascular Outcome: The Strong Heart Study J Am Coll Cardiol 2009; 54:1730-4; and Carmel M. McEniery, Yasmin, Barry McDonnell, Margaret Munnery, Sharon M. Wallace, Chloe V. Rowe, John R. Cockcroft, Ian B. Wilkinson, Central Pressure: Variability and Impact of Cardiovascular Risk Factors: The Anglo-Cardiff Collaborative Trial II Hypertension. 2008; 51:1-7. This difference is also important in the treatment of hypertension since different classes of antihypertensive drugs, for the same reduction in brachial systolic pressure, show substantial differences in reduction of central systolic pressure. See, Bryan Williams, Peter S. Lacy, Simon M. Thom, Kennedy Cruickshank, Alice Stanton, David Collier, Alun D. Hughes, H. Thurston, Differential Impact of Blood Pressure—Lowering Drugs on Central Aortic Pressure and Clinical Outcomes Principal Results of the Conduit Artery Function Evaluation (CAFE) Study Circulation. 2006; 113:1213-1225. Furthermore, traditional cuff brachial blood pressure devices do not measure the pressure waveform. The pressure waveform, especially the ascending aortic waveform, provides the physician insight into cardiovascular function, load and arterial stiffness not available from just brachial measurement of systolic and diastolic pressures.

The most common arterial site used as a surrogate to the aorta is the carotid artery. The carotid pressure waveform is similar in shape to the aortic pressure waveform given the carotid artery proximity to the aorta. A tonometer can be used to measure the carotid pressure non-invasively. However, it is technically difficult to record a high fidelity carotid pulse since the carotid location does not meet a number of the requirements for tonometric recordings (1). Thus, a high level of operator skill is required to obtain accurate carotid waveforms. In addition, the measured carotid waveform needs calibration, usually from a cuff blood pressure measurement on the brachial artery. Given that the brachial systolic pressure (SP) is different than the carotid SP and that both mean and diastolic pressure (MP and DP) is the same throughout the large, conduit arteries, the carotid pulse require measured brachial MP and DP to be calibrated. Since MP is not usually provided by conventional BP devices, MP is often estimated using an approximation equation using brachial SP and DP only ignoring the different shape and length of brachial pressure pulses. An accurate measure of brachial MP requires averaging the brachial pressure waveform where MP is dependent on contour of the pulse, not just its height. Hence an equation to estimate MP based only on pulse height may not produce an accurate value of MP. This would introduce error into the carotid pulse calibration so that the carotid pulse would not be an accurate measure of the aortic pressure.

Consequently, other non-invasive methods have been introduced, most prominently a method comprised of calculating the aortic pressure waveform from a noninvasive radial pressure tonometer measured waveform using a general transfer function representing the upper arm arterial system which does not change with age or gender, See O'Rourke U.S. Pat. No. 5,265,011. The transfer function represents the ratio of harmonics amplitude and phase of aortic to radial pressure waveforms. This method validated by the FDA had been implemented commercially and has been proved to be an accurate non-invasive method of estimating aortic pressure. See, Alfredo L. Pauca, Michael F. O'Rourke, Neal D. Kon, Prospective Evaluation of a Method for Estimating Ascending Aortic Pressure From the Radial Artery Pressure Waveform, Hypertension. 2001; 38:932-937; and James E. Sharman, Richard Lim, Ahmad M. Qasem, Jeff S. Coombes, Malcolm I. Burgess, Jeff Franco, Paul Garrahy, Ian B. Wilkinson, Thomas H. Marwick, Validation of a Generalized Transfer Function to Noninvasively Derive Central Blood Pressure During Exercise. Hypertension. 2006; 47:1203-1208. The proposed invention differs from this method by the use of a brachial cuff, which is similar to the one used in conventional cuff blood pressure measurement device, to derive the aortic pressure waveform instead of tonometer. Another advantage of the proposed invention is in the use on subjects with a fistula whose radial signal is undetectable.

Although the patent by O'Rourke (U.S. Pat. No. 5,265,011) proposed a general brachial to aortic pressure transfer function based on harmonics ratio to calculate aortic pressure, such a transfer function applies only to the brachial pressure waveform, not brachial arterial volume displacement waveform measured by a cuff. The volume waveform shape differs and is more dependent upon the cuff inflation pressure than the pressure waveform. This can lead to substantial differences in the shape of the two waveforms and, in turn, inaccurate measures of the mean pressure and characteristic waveform parameters. Furthermore, the O'Rourke patent did not address methods of obtaining the brachial pressure waveform non-invasively or the issues of using a surrogate easy-to-use, operator independent measurement for the brachial pulse. The proposed invention address these issues providing an easy to use method with appropriate transfer function or mathematical transformation for a brachial cuff volume waveform based on the cuff pressure.

A recent European patent application by Chen and Cheng (EP 2070472A1) discloses an oscillometric cuff volume waveform on the brachial artery to determine central aortic pressure using multi-regression analysis. The procedure accordingly requires recording oscillometric cuff volume waveform similar to the one used in electronic manometer blood pressure devices. The method requires that the cuff pulse be recorded after the cuff pressure is decreasing to a certain degree and during re-increasing of the cuff pressure. Second, the recorded cuff volume waveform is calibrated by mean and diastolic pressure. The patent mentions, in general, different methods based on multiple regression analysis to calculate central aortic systolic and diastolic pressure. One method uses multiple regression analysis from cuff pulse curve parameters as inputs to determine central systolic pressure.

There are many problems with the method proposed by Chen and Cheng in practice and theory. The method ignores the fact that the cuff volume waveforms morphology change depending on the difference between the cuff pressure and the subject's blood pressure, and not on the absolute value of the cuff pressure as proposed in that patent. Such differences would affect the brachial vascular unloading and cause changes in the pulse wave shape and size. This method does not indicate specifically the range of cuff pressures needed for recording a valid volume pulse. Without specifying that range of cuff pressures, the cuff volume waveform will have a different size and shape at different cuff pressure values. These differences in size and shape would, in turn, vary the cuff volume waveform parameters which are used to calculate central pressure. In some cases, these cuff waveform features used in the regression equation like second shoulder couldn't be identified. Furthermore regression equation accuracy and variation is dependent on the accuracy and variation of its parameters. Hence, central pressure estimated using the regression equation is susceptible to errors and variations in its many input parameters. These errors consequently affect the stability, consistency, and accuracy of the result.

Another patent application (US 2009/02870971 A1) by Lowe to calculate aortic pressure from a cuff volume waveform addresses the effect of the cuff pressure on the oscillometric cuff volume waveform. To stabilize the cuff volume waveform, the method proposes increasing the cuff pressure above systolic pressure by 25 mmHg, called suprasystolic pressure, and recording the cuff volume waveform. Through a series of assumptions regarding the changes in arterial diameter between brachial and subclavian root, an equation is formed that relates the pressure wave at the subclavian root to the brachial artery. The equation proposed to estimate aortic pressure from the measured cuff volume waveform at suprasystolic pressure in the brachial artery requires the assumption of four constants. One constant related to reflection coefficient at the occluded brachial arterial pulse, and another related to the travel time of the wave from the subclavian root to the cuff occlusion. The reconstructed aortic waveform resulting from that equation requires scaling, calibration or correction as a result of the effect of the pressure difference between the cuff and mean pressure and the effect of suprasystolic cuff pressure. As a result the other two constants, based on these factors, are needed to rescale the reconstructed waveform.

Although the method by Lowe is based on reasonable and solid theory, and the method already addresses the stability of the oscillometric cuff pulse by adjusting the cuff pressure above systole, the method suffers from being impractical in application and dependent on many assumptions that affect the accuracy of the aortic pressure estimation. The method requires the knowledge of four constants with no defined means to estimate these constants. It is not known if these constants, especially the two scaling constants, can be generalized to all populations regardless of age, gender, height or weight. In the patent application, these constants were chosen arbitrarily and the author suggested estimating them from an independent set of data determined from invasive recordings or through mathematical modeling ([0076] in Patent application US 2009/02870971 A1). Without such information, the method has limited application and produces erroneous results.

Furthermore, as pulses travel from the aorta to the periphery, the pulses change and amplify. The amplification is, in part, dependent on the pulses' harmonic content at the aorta and in the periphery. One factor that affects the pulse harmonic content is the length of the cardiac pulse, or heart rate. The equation proposed by Lowe to calculate aortic pulse from brachial cuff pulse does not consider the effect of heart rate, and hence, did not consider the harmonic amplification nature of the traveling pulse. For example, it is known through invasive studies and principles of cardiovascular hemodynamics that changes in heart rate alters pulse harmonics and consequently affect the amplification ratio from the aorta to the periphery (1). However, according to equation in Lowe's patent, pressure pulses with the same systolic and diastolic pressure but different heart rates would produce similar aortic pulse results whereas cardiovascular hemodynamics principles teach that the results should be different.

In addition to this fundamental issue, the measurement requires the occlusion of the brachial artery and cessation of the blood flow in the arm until proper waveforms are recorded which would be uncomfortable for the patient.

Another patent by Wasserttheuer WO 2007/053868, (PCT/AT2006/000457) proposes an equation to calculate cardiac output from the aortic pressure waveform which, in turn, is calculated from the brachial cuff pressure using neural network techniques, which is an algorithm very much dependent on the data set used to train it. In order to have a general neural network algorithm that can be applied to all populations, the training data needs to cover the complete range of possible brachial cuff pulses and corresponding aortic pulses. Pulses with all possible heart rates, shapes and pressure values need to be included in the training to have a general methodology.

The proposed invention methodology differs from the neural network in that it uses transfer functions based on harmonics ratio between the peripheral and central aortic waveforms where trends can be identified easily and consequently generalized to a larger population.

Even though harmonic amplification of waveforms along the arterial tree is well-established in cardiovascular hemodynamics, none of the prior art, except from the O'Rourke patent, addresses this significant issue. These methods don't show how changes in pressure pulse harmonics affect the calculated output. For example, a subjects' heart rate can vary considerably from one examination to another. This consequently alters the aortic pulses harmonics and affects the peripheral pulses harmonics. Any method that does not take heart rate and waveform morphology into account would fail in tests during drug intervention or any maneuvers that alter subject's pulse shape, pressure and heart rate, limiting the method's application and reducing its accuracy.

None of the prior art that uses the brachial cuff to sense a volume waveform addresses the fact that the volume waveform shape changes as cuff pressure changes in reference to the subject's blood pressure. Such changes would cause instability in all of these methods.

Also, these methods would introduce calibration-based errors because of the incorrect assumption that the oscillometric cuff volume waveform is a pressure pulse. None of these methods address this issue.

SUMMARY OF THE INVENTION

The present invention applies a general harmonic amplification transfer function estimated by either filter design or system identification techniques in either the frequency or time domain to establish an equation in frequency or time domain that mathematically transforms the brachial cuff volume waveform to an aortic pressure waveform over different cuff pressure ranges. The invention provides an easy to use, operator independent, accurate method to obtain aortic pressure from a cuff pulse taking into consideration the harmonic amplification nature of arterial pressure pulses and physiology behind arterial volume displacement pulses.

In one embodiment, the invention comprises the use of a brachial cuff device to record brachial cuff waveforms, normally a volumetric displacement waveform. The method begins by measuring brachial pressure using conventional oscillometric or auscultatory methods, e.g. the same brachial cuff can be used to measure the patient's SP and DP. The next step is to increase the cuff pressure to a value related to the measured brachial pressure. The invention preferably identifies three ranges of cuff pressure based on measured brachial SP and DP in which the shape of the cuff waveform can change significantly. The ranges are below DP, between SP and DP and above SP. The cuff pressure is inflated to a pressure value within one of these ranges. Pressure values near SP and DP may alter the shape of the waveform and should be avoided.

The cuff volume waveform is then calibrated either with brachial SP and DP, MP and DP, or MP and SP by equating with the waveform's maximum and minimum, mean and minimum, or mean and maximum respectively.

A generalized transfer function (e.g. FIG. 2A), that relates the amplitude and phase of the harmonics of aortic pressure waveform to the cuff volume waveform, is estimated beforehand from simultaneous recordings of cuff volume waveform and invasive (e.g. catheter) or an equivalent non-invasive (e.g. SphygmoCor) aortic pressure waveforms. The estimation preferably involves either frequency harmonics analysis or estimating coefficients for the time difference equation which may involve filter (finite or infinite impulse response) design technique or parametric model estimation methods (e.g. system identification methods). Since the cuff volume waveform typically changes in shape depending on the range where the cuff pressure lie, different transfer functions are estimated for each range. Therefore, depending on the cuff pressure, a suitable transfer function is applied on the cuff volume waveform to estimate high fidelity central aortic pressure waveform, where the waveform features are preserved and similar to the features in invasive or equivalent non-invasive aortic pressure waveforms.

As an alternative to using a generalized transfer function to convert the calibrated brachial cuff waveform directly to a calibrated aortic pressure waveform, it is possible to use intermediate transfer functions composed of arterial segment transfer functions like a brachial volume waveform to radial pressure or carotid pressure waveform transfer function plus a radial pressure or carotid pressure waveform to an aortic pressure waveform transfer function Since, depending on the cuff pressure, the cuff volume waveform differs in shape from brachial pressure waveform and since the mean of the cuff volume waveform therefore may eventually differ from the mean pressure (MP) which is similar at brachial and aorta arteries, the estimated aortic pressure waveform may require calibration adjustment. A calibration transfer function (e.g. FIG. 2B) transfers the amplitude of brachial cuff waveform into the amplitude of the aortic pressure waveform preserving the mean pressure equivalence between the two arterial locations. The resultant aortic amplitude is used to calibrate the estimated aortic pressure waveform. If MP is measured accurately through the brachial blood pressure device, a calibration transfer function may not be required.

Other aspects and features of the invention will be apparent to those of ordinary skill in the art upon reviewing the drawings and the following description thereof.

BRIEF DESCRIPTION OF THE DRAWINGS

FIG. 2A illustrates a brachial cuff to aortic pressure frequency transfer function and FIG. 2B illustrates a calibration transfer function, both in terms of amplitude and phase at PCuff=(50%)DP in accordance with a preferred embodiment of the invention.

DESCRIPTION OF THE DRAWINGS

Figure 1:
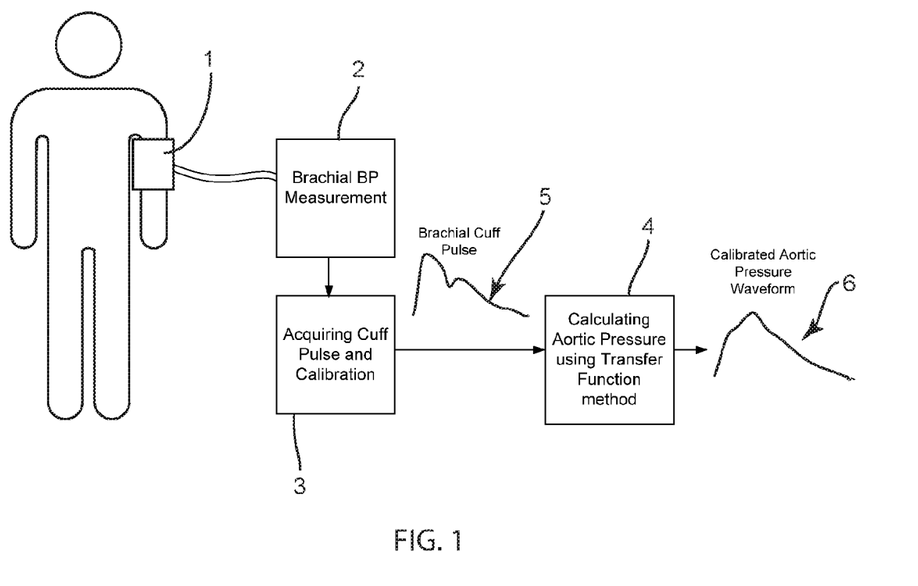
FIG. 1 is schematic drawing illustrating the main components of the invention.

As depicted in the diagram of FIG. 1, the invention involves the following basic steps:
  a) Measuring a patient's brachial pressure 1, 2, i.e., systolic and diastolic pressure (SP & DP respectively);
  b) Acquiring and calibrating a cuff pulse waveform 3; and
  c) Calculating a calibrated aortic pressure waveform 6 using one or more generalized transfer functions 4 from the calibrated brachial cuff waveform 5.

The steps a) and b) are preferably implemented in hardware and software, while step c) is preferably implemented in software.

Preferably, steps a) and b) comprise measuring brachial systolic and diastolic pressure or mean pressure through an oscillometric cuff method and acquiring the brachial cuff signal at specified cuff pressure. The step a) measurement can be made with a conventional blood pressure cuff device. The step b) measurement is preferably made with a device comprising a brachial cuff, a tube, a pressure pump with a control system, a pressure sensor and a digital signal processing (DSP) unit to prepare the cuff brachial signal for the software to calculate the aortic pressure waveform. The DSP unit may be connected to the computer implementing the software via a USB cable. The DSP unit may consist of an analog-to-digital component and low-pass, high pass filters and amplifiers. The cuff, the tube and the pump are similar to the components of conventional brachial blood pressure measurement devices. The control unit is used to maintain the cuff pressure within a predetermined pressure range. This is explained in more detail below.

Another embodiment of the invention comprises only step b) above. The brachial systolic and diastolic pressure is measured automatically by oscillometric methods or manually by auscultatory methods and used to set the cuff inflation pressure while acquiring the cuff volume waveform. Also, in this embodiment, the measured brachial SP and DP are used to calibrate the recorded cuff volume waveform so it can be used as input to the algorithm that calculates the aortic pressure waveform.

Methodology

The following methodology is implemented by the software. The main components adjust the cuff pressure and then use the calibrated brachial cuff waveform and transfer functions representing the harmonics ratio to determine the aortic pressure waveform. These two components are described below, followed by a description of steps in the methodology.

A) Cuff Pressure

After measuring the brachial SP and DP, the cuff pressure is inflated to a pressure that depends on the subject's blood pressure values. As previously explained the cuff volume waveform is a measurement of arterial volume displacement where its shape is dependent on the difference between cuff pressure and the subject's blood pressure. There are three cuff pressure ranges where cuff volume waveform shape will be altered. The three ranges are:

(i) $P_{Cuff} < DP_B$ (1)

(ii) $DP_B \leq P_{Cuff} < SP_B$ (2)

(iii) $P_{Cuff} \geq SP_B$ (3)

where $P_{Cuff}$ is the cuff pressure in mmHg, $SP_B$ and $DP_B$ are the brachial systolic and diastolic pressure, respectively.

Accordingly, whatever range is used, the algorithm uses a different transfer function. This is described in detail in the next section on the transfer function.

The cuff pressure value should avoid border line values like DP and SP, because subject's pressure tend to vary during an examination, and this variation may cause the cuff pressure to change ranges and affect the algorithm. For example, if the cuff pressure is set to equal DP, it would be considered in range (ii) but if the subject's DP increases slightly, the cuff pressure would be in range (i) requiring a different transfer function. To assure the stability of the signal and that cuff volume pulse is not altered in shape with variation in blood pressure values, the cuff pressure in should be either:

(i) $P_{Cuff} = (K\%)DP$ (4)

(ii) $P_{Cuff} = (K\%)(SP_B - DP_B) + DP_B$ (5)

(iii) $P_{Cuff} = [(K\%) + 1]SP_B$ (6)

where K % is a percentage that guarantee the cuff pressure to be away from borderline pressure like SP or DP, such that any variations in SP or DP would not change cuff pressure region. For example, K % can be from 10 to 90%.

B) Transfer Function

The core of the algorithm to estimate an aortic pressure waveform is the transfer function that converts a brachial volume pulse waveform measured by the cuff into an aortic pressure waveform. The transfer function represents the harmonic ratio in amplitude and phase between the two waves, and the equation of the transfer function can be written in a frequency or time domain format. One example form is a filter form in which have specific frequency response and can be represented in the time domain. The brachial cuff waveform to aortic pressure transfer function is determined beforehand from simultaneous recordings of cuff volume waveform and invasive (e.g. catheter) or an equivalent non-invasive (e.g. SphygmoCor) aortic pressure waveforms. The estimation involves either frequency harmonics analysis or estimating coefficients for the time difference equation which may involve filter (Finite or infinite impulse response) design technique or parametric model estimation methods (e.g. system identification methods). The transfer function can be represented and written in the following frequency domain format:

a) Amplitude $$|H_{b \to a}(f)| = \frac{|PW_a(f)|}{|PW_b(f)|} \quad (7)$$

b) Phase $$\angle H_{b \to a}(f) = \angle PW_a - \angle PW_b \quad (8)$$

where $H_{b \to a}(f)$ is the brachial cuff pulse waveform to aortic pressure wave transfer function in frequency domain, $PW_a$ is the frequency domain representation of the aortic pressure waveform, and $PW_b$ is the frequency domain representation of brachial volume pulse waveform measured by the cuff. The $\|$ symbol represents the amplitude of the frequency function, and the $\angle$ symbol represents the phase of the frequency function. In the time domain, the transfer function can be represented as an impulse response or a set of coefficients that when converted into frequency domain would be equivalent to $H_{b \to a}(f)$.

$$Im(t) \xrightarrow{FFT} H_{b \to a}(t) \quad (9)$$

where Im(t) is the impulse response in time domain and FFT is the fast Fourier transform.

The calculation of an aortic pressure waveform from a brachial volume waveform using the transfer function can be made in frequency or time domain. First in frequency domain, the aortic pressure in frequency can be calculated as:

$$PW_a(f) = H_{b \to a}(f) \times PW_b(f) \quad (10)$$

where $PW_a$ can be converted into an aortic pressure waveform in the time domain using the inverse fast Fourier transform (IFFT)

$$PW_b(f) \underset{FFT}{\overset{IFFT}{\rightleftarrows}} AoPW(t) \quad (11)$$

In the time domain, there are two ways to calculate an aortic pressure waveform. One uses the impulse response Im(t) as follows:

$$AoPW(t)=Im(t)*BrCW(t) \quad (12)$$

where BrCW(t) is the brachial volume pulse waveform measured by the cuff and * is the convolution operation.

A second way is to calculate an aortic pressure in the time domain using a set of filter coefficients, a's and b's, in a 'difference' equation $$AoPW(t)=b_0BrCW(t)+b_1BrCW(t-1)+ b_2BrCW(t-2)+\ldots+b_{nb}BrCW(t-nb)-a_1AoPW(t-1)-a_2AoPW(t-2)-\ldots-a_{na}AoPW(t-na) \quad (13)$$

where na and nb called the order of the filter equation and are the number of coefficients a's and b's respectively.

The estimation of all formats of the transfer function in the frequency domain ($H_{b \to a}(f)$) and time domain (Im(t) or coefficients a's and b's) is based on harmonic analysis of the simultaneous recording of the brachial volume pulse waveform measured by the cuff and the invasive or non-invasive equivalent aortic pressure waveform.

A brachial cuff pulse to aortic pressure pulse transfer function (TFb→a) can be composed of intermediary arterial segments transfer functions such that $$BrCW \xrightarrow{TF_{b \to Art}} ArtPW \xrightarrow{TF_{Art \to a}} AoPW \quad (14)$$

where Art is an intermediary artery like radial or carotid arteries, $TF_{b \to Art}$ is the brachial cuff pulse to the intermediary arterial location pressure pulse transfer function, $TF_{Art \to a}$ is the intermediary arterial location pressure pulse to aortic pressure pulse transfer function and ArtPW is the intermediary arterial pressure waveform.

Accordingly, multiple brachial volume pulse waveform to aortic pressure waveform transfer functions are estimated to be used for different embodiments of the invention.
 (a) Transfer function at $P_{Cuff}<DP_B$ ($TF_{P_{Cuff}<DP_B}$)
 (b) Transfer Function at $DP_B \leq P_{Cuff}<SP_B$ ($TF_{DP_B \leq P_{Cuff}<SP_B}$)
 (c) Transfer Function at $P_{Cuff} \geq SP_B$ ($TF_{P_{Cuff} \geq SP_B}$)
 (d) Transfer Function to calibrate the aortic pressure waveform ($TF_{Calibrate}$)

$TF_{Calibrate}$ is used to estimate aortic systolic and diastolic pressure only, not the aortic waveform. While the invention can be implanted by providing different transfer functions for converting the brachial volume pulse waveform to the aortic pressure waveform for each of the preselected pressure ranges for the brachial cuff, i.e. $P_{Cuff}<DP_B$, $DP_B \leq P_{Cuff}<SP_B$; and $P_{Cuff} \geq SP_B$. On the other hand, in many applications it is preferable to simply require that the brachial cuff be inflated to within a selected predetermined pressure range, such as $P_{Cuff}<DP_B$ and implement software with a generalized transfer function (e.g. $TF_{P_{Cuff}<DP_B}$) specific for the brachial cuff being below the diastolic pressure ($DP_B$). Alternatively, although not preferred, a system implementing the invention can include transfer functions for each of the predetermined pressure ranges, e.g. $P_{Cuff}<DP_B$; $DP_B \leq P_{Cuff}<SP_B$; and $P_{Cuff} \geq SP_B$ and can be programmed to select the appropriate transfer function depending on the brachial cuff pressure. As mentioned previously, FIG. 2A illustrates an example transfer function for converting the brachial cuff waveform to an aortic pressure waveform. The transfer function operates in the frequency domain in terms of amplitude and phase and it has been calculated for the brachial cuff pressure to equal 50% of the diastolic pressure ($P_{Cuff}=\frac{1}{2} DP$).

Figure 2:
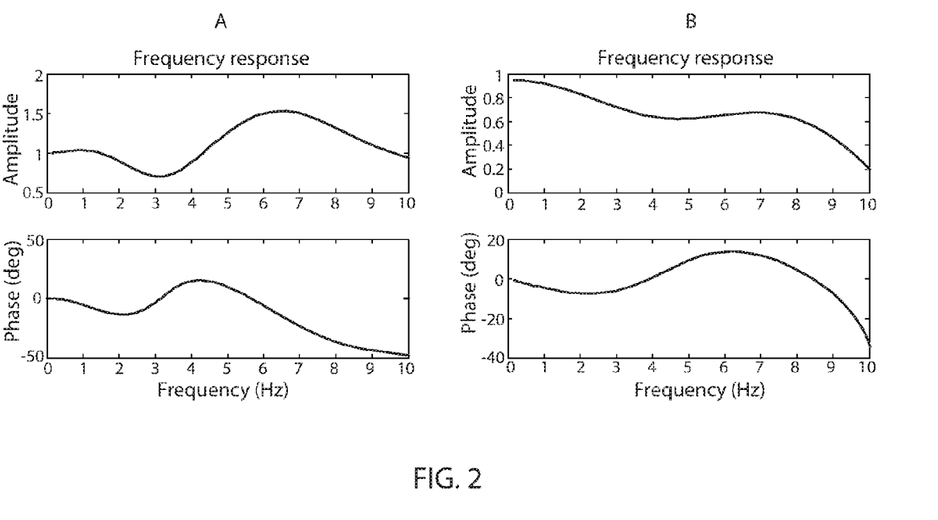
FIG. 2 illustrates exemplary generalized transfer functions.

The calibration transfer function ($TF_{Calibrate}$) converts the cuff pulse representing the brachial arterial volume displacement pulse to the pressure pulse. An example calibration transfer function is illustrated in FIG. 2B. If the cuff volume pulse was calibrated with the brachial SP and DP values, an error in the estimation of aortic systolic pressure (AoSP) would be introduced. The reason for the error is the difference in mean pressure MP between brachial volume pulse and aortic pulse when the brachial volume pulse is calibrated with the brachial SP and DP. Since MP should be the same at the two arterial locations, a calibration transfer function is added to reduce error in the estimation. Calibration TF may not be required in instances where MP is measured and used for calibration or where intermediary transfer functions are used.

C) Method Procedure

Figure 3:
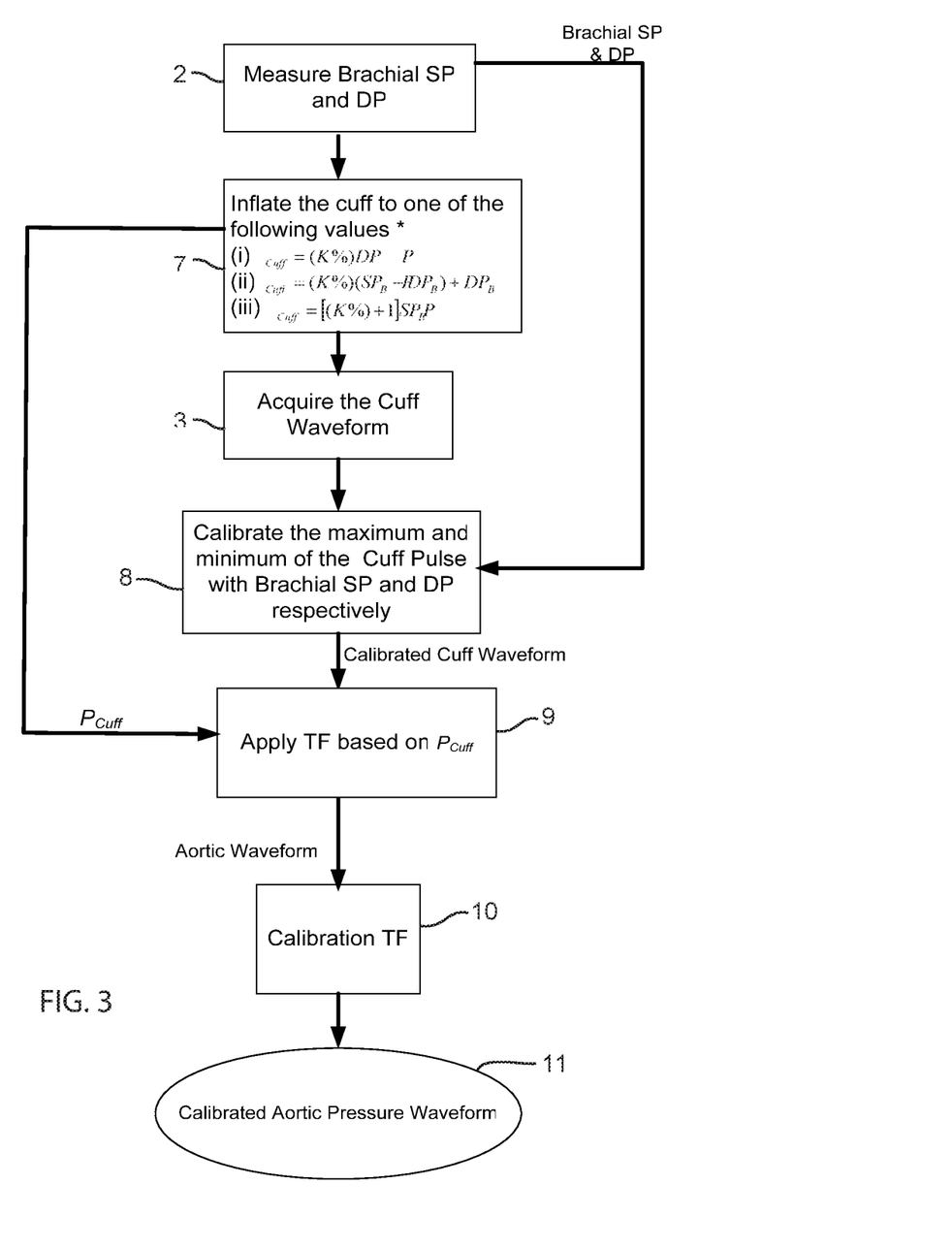
FIG. 3 is a flow chart illustrating the steps involved in one embodiment of the invention.

One embodiment of the invention follows the procedure illustrated in FIG. 3. Referring to FIG. 3, the procedure involves the following steps:
 a) Measure Brachial SP and DP using an automated oscillometric cuff blood pressure technique. See block labeled with reference number 2, FIG. 3.
 b) Inflate the cuff pressure to one of the following values. See block 7, FIG. 3.

$$P_{Cuff}=(K\%)DP \quad (i)$$

$$P_{Cuff}=(K\%)(SP_B-DP_B)+DP_B \quad (ii)$$

$$P_{Cuff}=[(K\%)+1]SP_B \quad (iii)$$

where K is a percentage that range preferably from 10 to 90%
 c) Acquire the cuff volume pulse measured by the pressure sensor in the hardware and processed through a DSP unit, block 3, FIG. 3.
 d) Calibrate the digitize cuff volume pulse signal maximum and minimum with measured brachial SP and DP respectively, block 8, FIG. 3.
 e) Apply one of the following transfer functions depending on the cuff pressure values of step b) above (see, block 7, FIG. 3) to convert the measured brachial cuff pulse waveform into aortic pressure waveform, see block 9, FIG. 3:

$$TF_{P_{Cuff}<DP_B} \quad (i)$$

$$TF_{DP_B \leq P_{Cuff}<SP_B} \quad (ii)$$

$$TF_{P_{Cuff} \geq SP_B}. \quad (iii)$$

Each of these transfer functions can be composed of intermediary transfer functions.
 f) Apply a calibration transfer function $TF_{Calibrate}$, see block 10, FIG. 3, if necessary to calibrate the calculated aortic pressure from block 9, FIG. 3.

Figure 4:
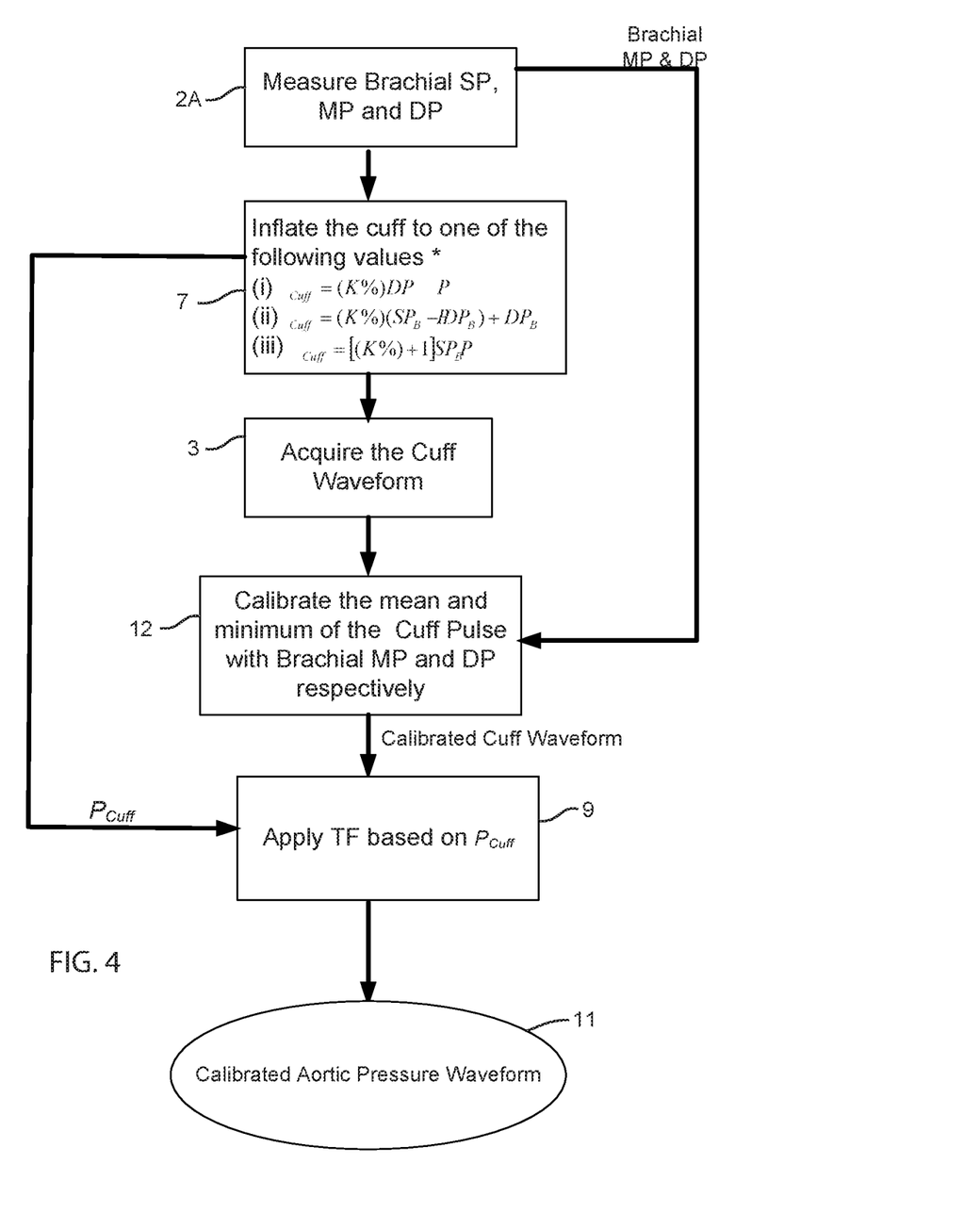
FIG. 4 is a flow chart illustrating steps involved in a second embodiment of the invention.

FIG. 4 illustrates another embodiment, where MP is measured and the calibration uses MP and DP. Referring to FIG. 4, this procedure involves the following steps:
 a) Measure the brachial SP, MP and DP using automated oscillometric cuff blood pressure technique, see block 2, FIG. 4.

b) Inflate the cuff pressure to one of the following values, see block 7, FIG. 4.

$$P_{Cuff}=(K\%)DP \quad \text{(i)}$$

$$P_{Cuff}=(K\%)(SP_B-DP_B)+DP_B \quad \text{(ii)}$$

$$P_{Cuff}=[(K\%)+1]SP_B \quad \text{(iii)}$$

where K is a percentage that range preferably from 10 to 90%.

c) Acquire the cuff pulse measured by the pressure sensor in the hardware and processed through a DSP unit, see block 3, FIG. 4.

d) Calibrate the digitize cuff pulse signal mean and minimum with measured brachial MP and DP, respectively, see block 12, FIG. 4.

e) Apply one of the following transfer functions depending on the cuff pressure values of step b) above (see block 7, FIG. 4) to convert the measured brachial cuff pulse waveform into aortic pressure waveform, see block 9, FIG. 4:

$$TF_{P_{Cuff}<DP_B} \quad \text{(i)}$$

$$TF_{DP_B \leq P_{Cuff} \leq SP_B} \quad \text{(ii)}$$

$$TF_{P_{Cuff} \geq SP_B} \quad \text{(iii)}$$

Each of these transfer functions can be composed of intermediary transfer functions.

Figure 5:
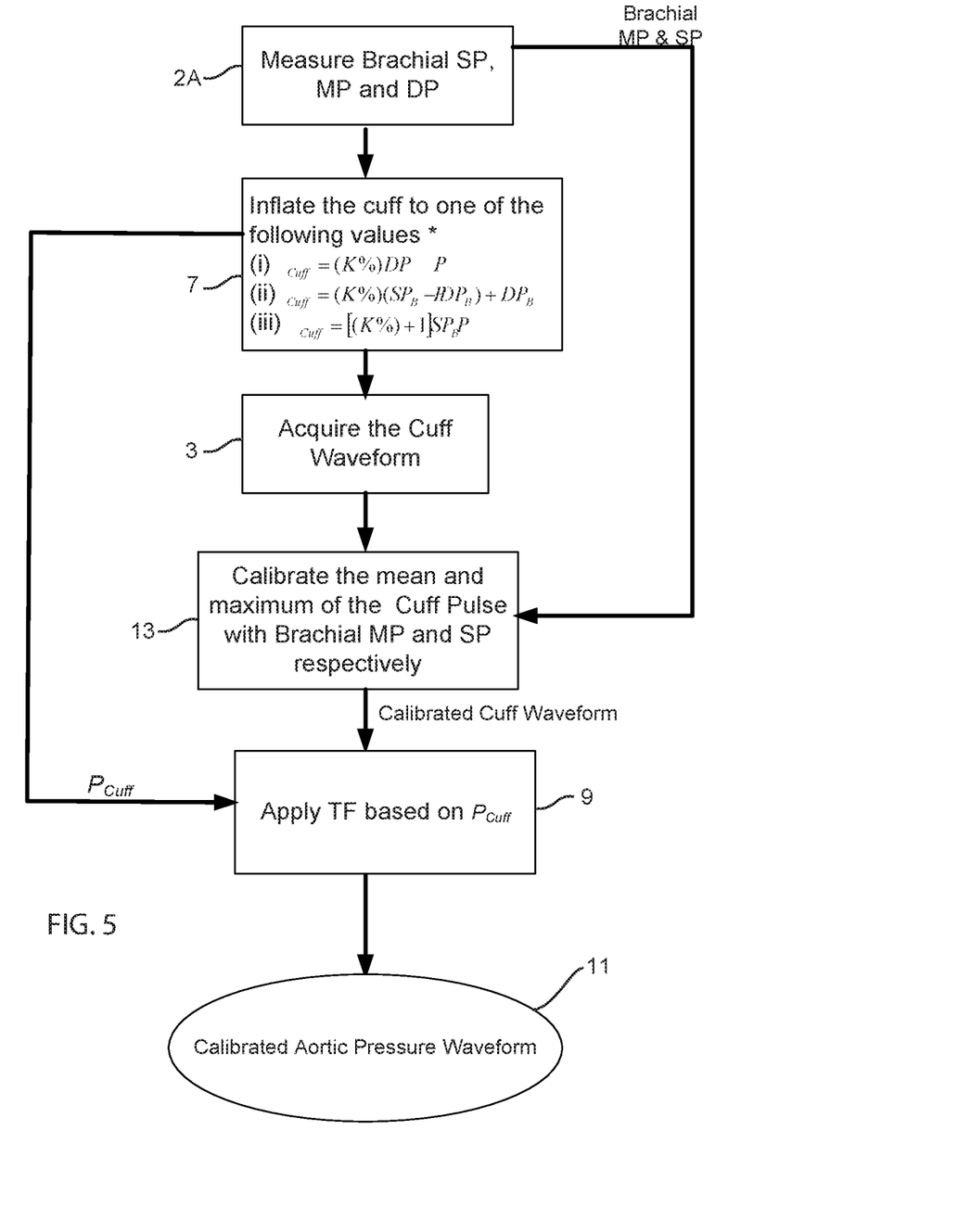
FIG. 5 is a flow chart illustrating the steps involved in a third embodiment of the invention.

FIG. 5 illustrates another embodiment, where MP is measured and the calibration uses MP and SP. Referring to FIG. 5, this procedure involves the following steps.

a) Measure Brachial SP, MP and DP using an automated oscillometric cuff blood pressure technique, see block 2, FIG. 5.

b) Inflate the cuff pressure to one of the following values, see block 7, FIG. 5.

$$P_{Cuff}=(K\%)DP \quad \text{(i)}$$

$$P_{Cuff}=(K\%)(SP_B-DP_B)+DP_B \quad \text{(ii)}$$

$$P_{Cuff}=[(K\%)+1]SP_B \quad \text{(iii)}$$

where K is a percentage that range from preferably 10 to 90% c) Acquire the cuff pulse measured by the pressure sensor in the hardware and processed through a DSP unit, see block 3, FIG. 5.

d) Calibrate the digitize cuff pulse signal mean and maximum with measured brachial MP and SP respectively, see block 13, FIG. 5.

e) Apply one of the following transfer functions depending on the cuff pressure values of step b) (see block 7, FIG. 5) to convert the measured brachial cuff pulse waveform into the aortic pressure waveform, see block 9, FIG. 5:

$$TF_{P_{Cuff}<DP_B} \quad \text{(i)}$$

$$TF_{DP_B \leq P_{Cuff} \leq SP_B} \quad \text{(ii)}$$

$$TF_{P_{Cuff} \geq SP_B} \quad \text{(iii)}$$

Each of these transfer functions can be composed of intermediary transfer functions.

Also, all these embodiments of the invention can be used with a stand-alone blood pressure measurement device where the brachial blood pressure values are entered manually.

In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps.

I claim:

1. A blood pressure measuring system for determining a calibrated aortic pressure waveform with cardiovascular waveform features preserved, the system comprising:

a brachial cuff device having a brachial cuff, a tube, a pressure pump with a control unit, and a pressure sensor that provides an analog signal, said brachial cuff device being capable of measuring a patient's brachial systolic pressure ($SP_B$) and brachial diastolic pressure ($DP_B$) by oscillometric technique;

the control unit controlling the inflation of the brachial cuff around a patient's upper arm to a constant pressure within a predetermined pressure range, wherein the predetermined pressure range is one of less than the patient's brachial diastolic pressure $DP_B$ as measured by the brachial cuff device by oscillometric technique, between the patient's brachial diastolic pressure $DP_B$ and the brachial systolic pressure $SP_B$ as measured by the brachial cuff device by oscillometric technique, and above the patient's brachial systolic pressure $SP_B$ as measured by the brachial cuff device by oscillometric technique;

a digital signal processor comprising a low pass filter and a high pass filter that receives the analog signal from the pressure sensor when the cuff pressure is maintained at a constant pressure within the predetermined pressure range and outputs a digital brachial cuff signal containing filtered data that preserves cardiovascular waveform features of the patient's brachial cuff volumetric displacement waveform; and software on a computer that calibrates the brachial cuff volumetric displacement waveform using at least two of the patient's brachial systolic pressure ($SP_B$) as measured by the brachial cuff device by oscillometric technique, the patient's brachial mean pressure ($MP_B$) and the patient's brachial diastolic pressure ($DP_B$) as measured by the brachial cuff device by oscillometric technique, wherein the patient's brachial mean pressure ($MP_B$) if used is calculated by the brachial cuff device based on measured values for the patient's brachial systolic pressure ($SP_B$) and the patient's brachial diastolic pressure ($DP_B$), and the software further converts the calibrated brachial cuff volumetric displacement waveform with cardiovascular waveform features preserved to a calibrated aortic pressure waveform with cardiovascular waveform features preserved by using one or more generalized transfer functions, wherein one or more generalized transfer functions comprise at least a first generalized transfer function that transforms the calibrated brachial cuff waveform to an intermediate artery pressure waveform and a second generalized transfer function that transforms the intermediate artery pressure waveform to an aortic pressure waveform;

wherein each of the one or more generalized transfer functions are determined specifically for application to a calibrated brachial cuff volumetric displacement waveform measured by the brachial cuff inflated to a pressure within the predetermined pressure range, said one or more generalized transfer functions representing the harmonic ratio in amplitude and phase to transform the calibrated brachial cuff volumetric displacement waveform with cardiovascular waveform features preserved to the calibrated aortic pressure waveform with cardiovascular waveform features preserved when the brachial cuff is inflated to a pressure within the selected pressure range.

2. A blood pressure measuring system as recited in claim 1 wherein software also uses a generalized calibration transfer function to reduce error in the estimation of aortic systolic pressure, which would be introduced by calibrating the cuff volume pulse with the measured brachial $SP_B$ and $DP_B$ values.

3. A blood pressure measuring system as recited in claim 1 wherein the predetermined pressure range is 10-90% of the diastolic pressure ($DP_B$).

4. A blood pressure measuring system as recited in claim 1 further comprising multiple generalized transfer functions each being based on cuff pressures within a predetermined pressure range.

5. A blood pressure measuring system as recited in claim 1 wherein the predetermined pressure range is between $SP_B$ and $DP_B$ and cuff pressure is defined by the following equation $$P_{Cuff}=(K\%)(SP_B-DP_B)+DP_B$$

where K % is chosen to be between 10 and 90%.

6. A blood pressure measuring system as recited in claim 1 wherein the predetermined pressure range is above $SP_B$ and the cuff pressure is in the following range $$P_{Cuff}=[(K\%)+1]SP_B$$

where K % ranges from 10 to 90%.

7. A blood pressure measuring system as recited in claim 1 wherein the calibrated brachial cuff waveform that is converted using one or more generalized transfer functions to the calibrated aortic pressure waveform with its cardiovascular waveform features preserved comprises an average of multiple recorded and calibrated brachial cuff waveforms measured by the inflated cuff around the patient's upper arm.

8. In a blood pressure measuring system, a method for determining a calibrated aortic pressure waveform having cardiovascular waveform features preserved, the method comprising the steps:

providing an inflatable brachial cuff having a pressure sensor to measure pressure within the brachial cuff, said pressure sensor outputting an analog signal;

providing a digital signal processor that receives the analog signal from the pressure sensor and is configured to output a digital brachial cuff signal containing filtered digital data that preserves the cardiovascular waveform features of the patient's brachial cuff volumetric displacement waveform;

measuring at least the patient's brachial systolic pressure ($SP_B$) and brachial diastolic pressure ($DP_B$) using the brachial cuff in an oscillometric mode;

inflating the brachial cuff around a patient's upper arm to a constant pressure that is between the measured $DP_B$ and the measured $SP_B$;

maintaining the brachial cuff at said constant pressure and acquiring the analog signal from the cuff pressure sensor;

filtering and converting the acquired analog signal to generate filtered digital data that preserves the cardiovascular waveform features of the patient's brachial cuff volumetric displacement waveform, and recording the filtered data that preserves the cardiovascular waveform features of the patient's brachial cuff volumetric displacement waveform;

using at least two of brachial systolic pressure ($SP_B$), brachial mean pressure ($MP_B$) and brachial diastolic pressure ($DP_B$) to calibrate the recorded brachial cuff waveform, wherein brachial mean pressure ($MP_B$), if used, is determined from the measured brachial systolic pressure ($SP_B$) and the measured brachial diastolic pressure ($DP_B$); and using one or more generalized transfer functions to convert the calibrated, recorded brachial cuff waveform to a calibrated aortic pressure waveform having its cardiovascular waveform features preserved, wherein said one or more generalized transfer functions represent the harmonic ratio in amplitude and phase to transform the calibrated brachial cuff volumetric displacement waveform having cardiovascular waveform features preserved to the calibrated aortic pressure waveform having cardiovascular waveform features preserved when the brachial cuff is inflated to a pressure between the patient's measured diastolic pressure ($DP_B$) and the patient's measured systolic pressure ($SP_B$) and further wherein one or more generalized transfer functions comprise at least a first generalized transfer function that mathematically transforms the calibrated brachial cuff waveform to an intermediate artery pressure waveform and a second generalized transfer function that transforms the intermediate artery pressure waveform to an aortic pressure waveform.

9. A method as recited in claim 8 further comprising the step of displaying the calibrated aortic pressure waveform as a trace or otherwise on a computer display screen.

10. A method for determining a calibrated aortic pressure waveform as recited in claim 8 wherein the brachial cuff is inflated around the patient's upper arm to a constant pressure that is defined by the following equation $$P_{Cuff}=(K\%)(SP_B-DP_B)+DP_B$$

where K % is chosen to be between 10% and 90%.

11. A method of determining a calibrated aortic pressure waveform as recited in claim 8 wherein the one or more generalized transfer functions are estimated from simultaneously recorded data for a general population.

12. A method as recited in claim 8 wherein the calibrated brachial cuff waveform that is converted using one or more generalized transfer functions to the calibrated aortic pressure waveform with its cardiovascular waveform features preserved comprises an average of multiple recorded and calibrated brachial cuff waveforms measured by the inflated cuff around the patient's upper arm.

13. A method of determining a calibrated aortic pressure waveform as recited in claim 8 wherein the brachial cuff is part of a device that comprises the brachial cuff, a tube, a pressure pump with a pressure control system, and a pressure sensor that provides an analog signal and the blood pressure measuring system further comprises the digital signal processor that has a low pass filter and a high pass filter, receives the analog signal from the pressure sensor and outputs a digital brachial cuff signal containing filtered data preserving the cardiovascular waveform features of patient's brachial cuff volumetric displacement waveform, and a computer that receives the digital brachial cuff signal, records and calibrates the brachial cuff waveform, and converts the calibrated brachial cuff waveform to the calibrated aortic pressure waveform having cardiovascular waveform features preserved using said one or more generalized transfer functions representing the harmonic ratio in amplitude and phase to transform a calibrated brachial cuff volumetric displacement waveform having cardiovascular waveform features preserved to the calibrated aortic pressure waveform having cardiovascular waveform features preserved when the brachial cuff is inflated to a pressure between the patient's measured diastolic pressure ($DP_B$) and the patient's measured systolic pressure ($SP_B$).

14. A method of determining a calibrated aortic pressure waveform as recited in claim 8 wherein the calibrated, recorded brachial cuff waveform that is converted to a calibrated aortic pressure waveform having its cardiovascular waveform features preserved is an average of multiple calibrated, recorded brachial cuff waveforms.

15. A method of determining a calibrated aortic pressure waveform as recited in claim 8 wherein the one or more generalized transfer functions are implemented by software on a computer.

* * * * *